US010724032B2

(12) United States Patent
DeJohn et al.

(10) Patent No.: US 10,724,032 B2
(45) Date of Patent: Jul. 28, 2020

(54) SAMPLE EXTRACTION AND PREPARATION DEVICE

(71) Applicant: Biomeme, Inc., Philadelphia, PA (US)

(72) Inventors: Marc Dominic DeJohn, Philadelphia, PA (US); Jesse Wilson vanWestrienen, Philadelphia, PA (US)

(73) Assignee: BIOMEME, INC., Philadelphia, PA (US)

( * ) Notice: Subject to any disclaimer, the term of this patent is extended or adjusted under 35 U.S.C. 154(b) by 115 days.

(21) Appl. No.: 15/682,675

(22) Filed: Aug. 22, 2017

(65) Prior Publication Data

US 2018/0105810 A1     Apr. 19, 2018

Related U.S. Application Data

(63) Continuation of application No. 14/530,449, filed on Oct. 31, 2014, now Pat. No. 9,926,553.

(Continued)

(51) Int. Cl.
| | | |
|---|---|---|
| *C12N 15/10* | (2006.01) | |
| *B01L 3/02* | (2006.01) | |
| *B01L 3/00* | (2006.01) | |

(52) U.S. Cl.
CPC ........ *C12N 15/1017* (2013.01); *B01L 3/0217* (2013.01); *B01L 3/502* (2013.01);
(Continued)

(58) Field of Classification Search
CPC ... C12N 15/1017; B01L 3/0217; B01L 3/502; B01L 2200/0631; B01L 2300/0681; B01L 2400/0478; B01L 2400/049
(Continued)

(56) References Cited

U.S. PATENT DOCUMENTS

| | | |
|---|---|---|
| 3,757,780 A | 9/1973 | Ishikawa |
| 5,151,192 A | 9/1992 | Matkovich et al. |
| | (Continued) | |

FOREIGN PATENT DOCUMENTS

| | | |
|---|---|---|
| CN | 101722071 A | 6/2010 |
| EP | 0471721 B1 | 4/1995 |
| | (Continued) | |

OTHER PUBLICATIONS

Notice of allowance dated Jan. 2, 2018 for U.S. Appl. No. 14/530,449.
(Continued)

*Primary Examiner* — Benjamin R Whatley
*Assistant Examiner* — Jacqueline Brazin
(74) *Attorney, Agent, or Firm* — Wilson, Sonsini, Goodrich & Rosati PC

(57) ABSTRACT

A fluid sample extraction device is disclosed comprising a housing defining an internal fluid passage having a distal open end and a proximal open end and a porous medium within the fluid passage, between the distal open end and proximal open end. The porous medium, which may be glass, is configured to allow fluid flow in the fluid passage to flow around the porous medium, toward the proximal open end of the housing, when fluid is drawn from the distal open end toward the proximal open end, and to allow fluid in the fluid passage to flow toward the distal open end of the housing, through the porous medium when the fluid is forced toward the distal open end. The porous medium is also configured to capture nucleic acids in the porous medium from the fluid when fluid is forced through the porous medium. Devices and kits are also disclosed.

26 Claims, 13 Drawing Sheets

Related U.S. Application Data

(60) Provisional application No. 61/898,873, filed on Nov. 1, 2013.

(52) U.S. Cl.
  CPC ............... *B01L 2200/0631* (2013.01); *B01L 2300/0681* (2013.01); *B01L 2400/049* (2013.01); *B01L 2400/0478* (2013.01)

(58) Field of Classification Search
  USPC ......................................................... 422/527
  See application file for complete search history.

(56) References Cited

U.S. PATENT DOCUMENTS

| | | | |
|---|---|---|---|
| 5,626,567 | A | 5/1997 | Gmeiner |
| 5,849,488 | A | 12/1998 | Alatossava et al. |
| 6,274,371 | B1 | 8/2001 | Colpan |
| 7,759,112 | B2 | 7/2010 | Belgrader |
| 8,454,892 | B1 | 6/2013 | Rychwalski et al. |
| 9,926,553 | B2 | 3/2018 | De et al. |
| 2001/0007062 | A1* | 7/2001 | Dumaresq-Lucas ......... A61M 5/3145 604/236 |
| 2002/0150907 | A1* | 10/2002 | Fomovskaia ...... C12N 15/1017 435/5 |
| 2006/0216206 | A1* | 9/2006 | Hudson ............. B01J 20/28042 422/534 |
| 2008/0145848 | A1 | 6/2008 | Stephan et al. |
| 2008/0145858 | A1 | 6/2008 | Kim et al. |
| 2009/0111193 | A1 | 4/2009 | Cooney et al. |
| 2011/0076735 | A1* | 3/2011 | Jovanovich ......... B01F 11/0071 435/173.3 |
| 2011/0201099 | A1 | 8/2011 | Anderson et al. |
| 2012/0288897 | A1 | 11/2012 | Ching et al. |
| 2013/0078619 | A1 | 3/2013 | Cooney et al. |
| 2014/0008311 | A1* | 1/2014 | Weston ............. B01D 29/0072 210/808 |
| 2015/0024436 | A1 | 1/2015 | Eberhart et al. |
| 2015/0126724 | A1 | 5/2015 | De et al. |
| 2016/0069921 | A1 | 3/2016 | Holmes et al. |
| 2016/0115520 | A1 | 4/2016 | Krishnamurthy |
| 2016/0155120 | A1 | 6/2016 | Hurry |

FOREIGN PATENT DOCUMENTS

| | | |
|---|---|---|
| EP | 0781291 B1 | 12/2004 |
| EP | 2174715 A1 | 4/2010 |
| EP | 2695629 A2 | 2/2014 |
| GB | 2344526 A | 6/2000 |
| TW | 207958 B | 6/1993 |
| TW | 201144037 A | 12/2011 |
| WO | WO-2009036956 A1 | 3/2009 |
| WO | WO-2012138177 A2 | 10/2012 |
| WO | WO-2013010178 A1 | 1/2013 |
| WO | WO-2013052318 A1 | 4/2013 |
| WO | WO-2015066540 A1 | 5/2015 |
| WO | WO-2019055875 | 3/2019 |
| WO | WO-2019143812 A1 | 7/2019 |

OTHER PUBLICATIONS

U.S. Appl. No. 14/530,449 Notice of Allowance dated Jan. 30, 2018.
European search report and search opinion dated Jun. 22, 2017 for EP Application No. EP14859198.5.
International preliminary report on patentability and search report dated Dec. 3, 2015 for PCT Application No. PCT/US14/63552.
Office action dated Mar. 25, 2016 for U.S. Appl. No. 14/530,449.
Office action dated Jun. 20, 2017 for U.S. Appl. No. 14/530,449.
Office action dated Aug. 10, 2016 for U.S. Appl. No. 14/530,449.
International Search Report and Written Opinion dated Apr. 2, 2019 for PCT/US1851228.
ISR/WO dated Apr. 19, 2019 for PCT/US18/064736.
ISR/WO dated May 23, 2019 for PCT/US19/14005.

* cited by examiner

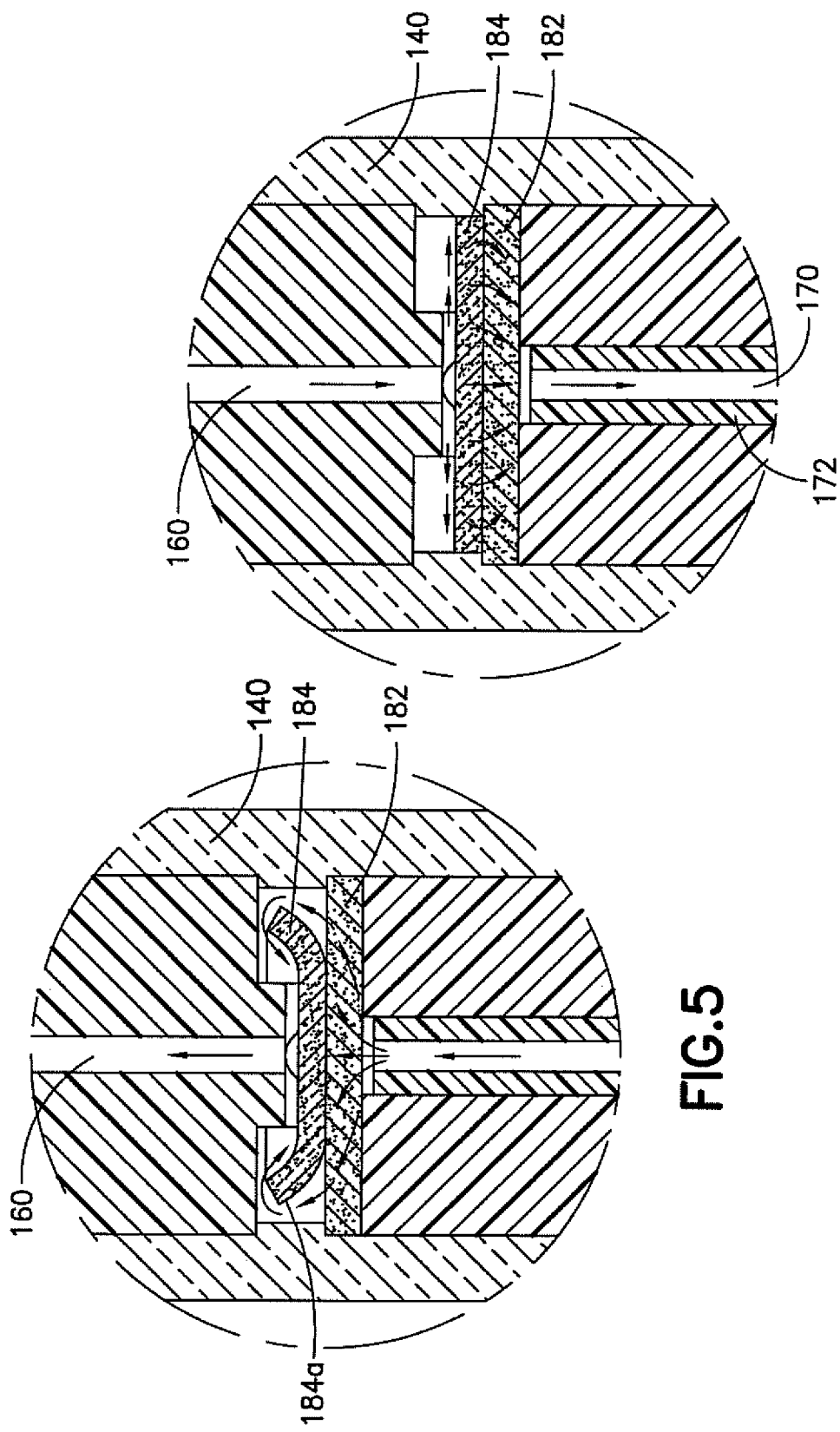

SAMPLE EXTRACTION AND PREPARATION DEVICE

RELATED APPLICATION

The present application is continuation of U.S. patent application Ser. No. 14/530,449 filed on Oct. 31, 2014, which claims the benefit of U.S. Provisional Patent Application No. 61/898,873 filed on Nov. 1, 2013, the entire contents of each of which are incorporated herein by reference.

FIELD OF THE INVENTION

A sample preparation device and, more particularly, a sample preparation device for biological fluid samples, such as nucleic acids, including a compliant medium that captures nucleic acids and acts as a check valve allowing the fluid sample to flow into the device, around the medium, and forcing the fluid sample through the medium as the sample fluid is discharged from the device.

BACKGROUND OF THE INVENTION

Sample preparation devices for the extraction of nucleic acids from biological samples in accordance with the Boom method, or variations thereof, are known.

In the Boom method, nucleic acids (DNA and RNA) are extracted from biological samples by the binding of the nucleic acids to silica beads in the presence of chaotropic agents. The biological samples may be whole blood, blood serum, buffy coat (a density gradient centrifuged fraction of an anticoagulated blood sample containing white blood cells and platelets), urine, feces, cerebrospinal fluid, sperm, saliva, body tissues, nasal swabs, buccal swabs, cell cultures, food products, environmental water, soil, and vaccines, for example.

The chaotropic agents disrupt and denature the structure of the nucleic acids by interfering with the macromolecular interactions mediated by non-covalent forces, such as hydrogen bonding, van der Waals forces, and hydrophobic interactions, for example. In the presence of the chaotropic agents, water is removed from the phosphate groups of the nucleic acids, exposing them and allowing hydrophobic bonding to the silica. Protein, cellular debris, and other substances in the biological samples do not bond to the silica and are retained in the solution. Magnetic beads coated with silica may be used to assist in the separation of the nucleic acids bound to the silica coating from the solution.

In accordance with the Boom method, a biological sample is lysed and/or homogenized by mixing the biological sample with detergent in the presence of protein degrading enzymes. The chaotropic agents and silica or silica coated beads are mixed with the lysed biological sample, allowing nucleic acids to bond to the silica or silica coated beads. The silica beads are washed several times to remove non-nucleic acid materials, such as proteins, lipids, cellular constituents, including cellular molecules, and other substances found in biological samples. The nucleic acids are then eluted into a buffer from the silica or silica coated beads by decreasing the concentration of the chaotropic agents. The elution buffer may be pure water or Tris EDTA ("TE") buffer for example.

U.S. Patent Publication No. 2009/0111193 A1 describes a sample preparation device including a housing defining a passage and a filter of monolith absorbent that binds nucleic acids passing through the filter. The monolith absorbent may be a glass frit, a porous glass monolith, or porous monolithic polymers. The glass frit may be sintered glass of crushed beads. Pore sizes may vary from about 2 microns to about 220 microns. One end of the housing has a pipette tip. Samples are drawn into the housing through the pipette tip by an electronic pipetter device such as an electronic pipetter or robotic pipetting station. The electronic pipetter draws the sample through the filter. The nucleic acids bonded to the filter are washed with ethanol and eluted by an elution buffer. The eluted nucleic acids are quantified by polymerase chain reaction ("PCR").

The use of pipettes and electronic pipette devices is expensive. In addition, because of the large pore size, capture efficiency in U.S. Patent Application No. 2009/0111193A1 may be low and draw and discharge may be slow.

SUMMARY OF THE INVENTION

An inexpensive, rapid system for capturing nucleic acids from biological samples would be advantageous.

In accordance with an embodiment of the invention, a fluid sample device for extracting nucleic acids is disclosed comprising a housing defining a fluid passage and a porous medium within a fluid passage. A syringe or other devices may be used to draw a fluid sample into the housing and through the fluid passage, and to discharge the fluid sample from the fluid passage and housing. The porous medium is in a first position blocking the fluid passage. The porous medium flexes, moves, or is moved to a second position that at least partially unblocks the fluid passage, as a biological fluid sample is drawn through the passage, bypassing the medium. The porous medium returns to the first position blocking the fluid passage when the fluid sample is discharged from the housing through the passage, so that the fluid sample passes through the porous medium. Nucleic acids in the sample are captured by the porous medium, while the remainder of the fluid sample exits the housing. The porous medium may comprise silica or borosilicates, for example.

In one example, the porous medium is a compliant porous medium that flexes under the force of the fluid flow and vacuum created within the housing. While the fluid is drawn into the device. In another example, the porous medium is tilted or moved by the force of the fluid flow, as the fluid is drawn into the device. If titled or moved, the porous medium may be compliant or non-compliant.

In another example the porous medium may be in the form of a ball or other shaped product that bears against an opening in the fluid passage under the force of a spring, for example, to close the passage. The force of the fluid flow drawn into the housing and the vacuum force created by withdrawal of a plunger of the syringe, for example, overcome the force of the spring, moving the porous medium out of the opening, allowing fluid flow through the opening, around the medium. When fluid is discharged from the housing, the porous medium moves back into a position blocking the opening so that the fluid flows through the medium.

The porous medium thereby also acts as a check valve allowing fluid to flow rapidly through the passage, around the medium under a low pressure draw into the housing and requiring the fluid to flow through the medium as the fluid is discharged through the housing under higher pressure. Discharge pressure will be substantially greater than the drawing pressure, such as about five (5) times larger or more, for example, to force the fluid through the porous medium. Draw pressure by a syringe may be up to about 14 psi and discharge pressure by the syringe may be about 100 psi or more, for example.

The porous medium may comprise compliant glass fiber, such as a borosilicate glass fiber, for example. The fluid sample may be drawn into the housing and discharged from the housing by a manually operated syringe, for example. Other techniques may be used to draw and discharge the fluid sample through the passage as well, such as electronic or manual pipettes. The compliant medium may be supported by a porous, rigid support, such as a porous plastic media, for example. In another example, the compliant medium may be supported by a fiber plastic screen within the housing or another internal surface of the housing.

In accordance with an embodiment of the invention, a fluid sample extraction device is disclosed comprising a housing defining an internal fluid passage having a distal open end and a proximal open end and a porous medium within the fluid passage, between the distal open end and proximal open end. The porous medium is configured to allow fluid flow in the fluid passage to flow around the porous medium, toward the proximal open end of the housing, when fluid is drawn from the distal open end toward the proximal open end, and to allow fluid in the fluid passage to flow toward the distal open end of the housing, through the porous medium when the fluid is forced toward the distal open end. The porous medium is also configured to capture nucleic acids in the porous medium from the fluid when fluid is forced through the porous medium.

In accordance with another embodiment of the invention, a fluid sample extraction device comprises a housing comprising a proximal portion defining a proximal fluid passage, a proximal open end to the proximal fluid passage, and a proximal recessed region and a distal portion defining a distal fluid passage, a distal open end to the distal fluid passage, and a second recessed region. The proximal portion and the distal portion are coupled to each other so that the proximal recessed region and the distal recessed region form an internal chamber, and the proximal fluid passage and the distal fluid passage are in fluid communication with the internal chamber. The device further comprises a porous medium within the chamber. The porous medium is configured to move, at least in part, in a first direction, toward the proximal end, to allow fluid flow around the porous medium, toward the proximal fluid passage, when fluid is drawn toward the proximal fluid passage and move, at least in part, in a second direction, toward the distal end, to cause fluid flow from the chamber, through the porous medium, when the fluid is discharged from the chamber through the porous medium, into the distal fluid passage. The porous medium is also configured to capture nucleic acids in the fluid when fluid is discharged through the porous medium. The proximal open end is configured to be coupled to a pressure source.

In accordance with another embodiment of the invention, a method of extracting materials from a fluid comprises drawing fluid into fluid channel of a housing from a biological fluid sample, around a porous medium in the fluid channel, discharging the fluid from the fluid channel, through the porous medium, and capturing nucleic acids in the fluid in the porous medium while discharging the fluid sample from the housing.

In accordance with another embodiment of the invention, a method of extracting materials from a fluid sample is disclosed comprising drawing a fluid into a fluid channel of a housing from a fluid sample, opening a check valve in the fluid channel, the check valve comprising a porous medium, discharging the fluid from the fluid channel, closing the check valve, so that the discharging fluid is forced through the porous medium, and capturing a material from the fluid sample in the porous medium while discharging the fluid sample from the housing.

In accordance with another embodiment of the invention, a kit for extracting materials from a fluid sample comprises a syringe and an extraction device comprising a housing defining an internal fluid passage having a distal open end and a proximal open end. A porous medium is within the fluid passage, between the distal open end and proximal open end. The porous medium is configured to allow fluid flow around the porous medium, toward the proximal open end of the housing, when fluid is drawn from the distal open end toward the proximal open end, and to allow fluid to flow toward the distal open end of the housing, through the porous medium when the fluid is forced toward the distal open end. The porous medium is also configured to capture nucleic acids in the porous medium from the fluid when fluid is forced through the porous medium.

In accordance with another embodiment of the invention, a fluid sample extraction device comprises first means for defining an internal fluid passage having a distal open end and a proximal open end and second means in the fluid passage for: allowing fluid flow toward the proximal open end of the of the first means, around the second means, when fluid is drawn toward the proximal open end, allowing fluid flow toward the distal open end of the first means, through the second means when the fluid is forced toward the distal open end, and capturing nucleic acids from the fluid when fluid is forced through the second means.

BRIEF DESCRIPTION OF THE DRAWINGS

FIG. 5 is an enlarged view of an internal chamber of the extraction device, when sample fluid is drawn into the device FIG. 6 is an enlarged view of the internal chamber of the extraction device, when sample fluid is discharged through the medium;

DESCRIPTION OF THE PREFERRED EMBODIMENTS

Figure 1:
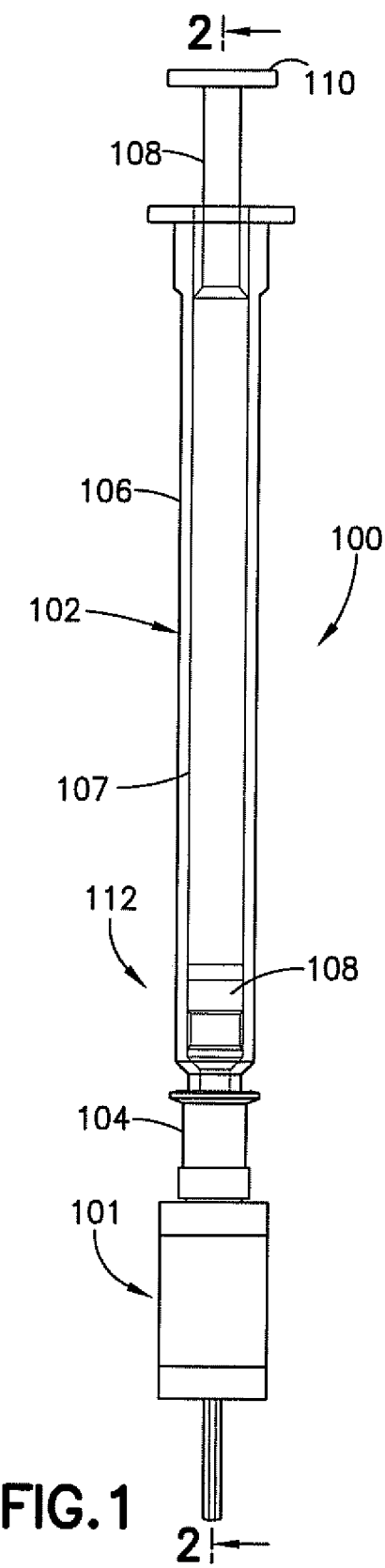
FIG. 1 is a side view of an example of a nucleic acid extraction ("NAE") device in accordance with an embodiment of the invention, coupled to a syringe.
Figure 2:
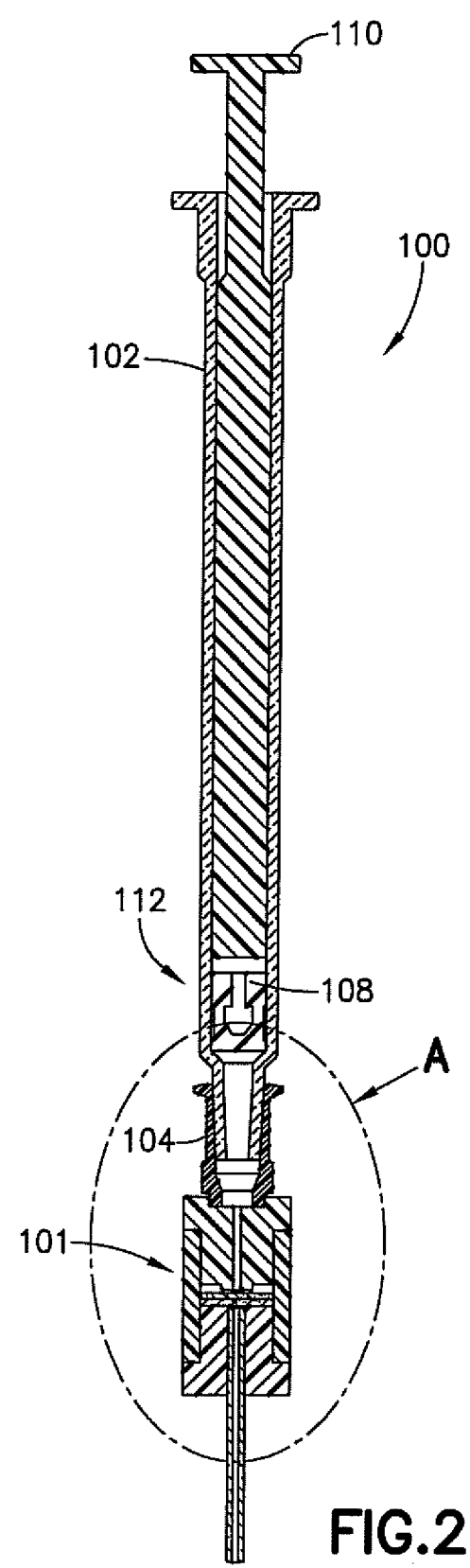
FIG. 2 is a cross-sectional view of the NAE device of FIG. 1, through line 2-2 of FIG. 1.
Figure 3:
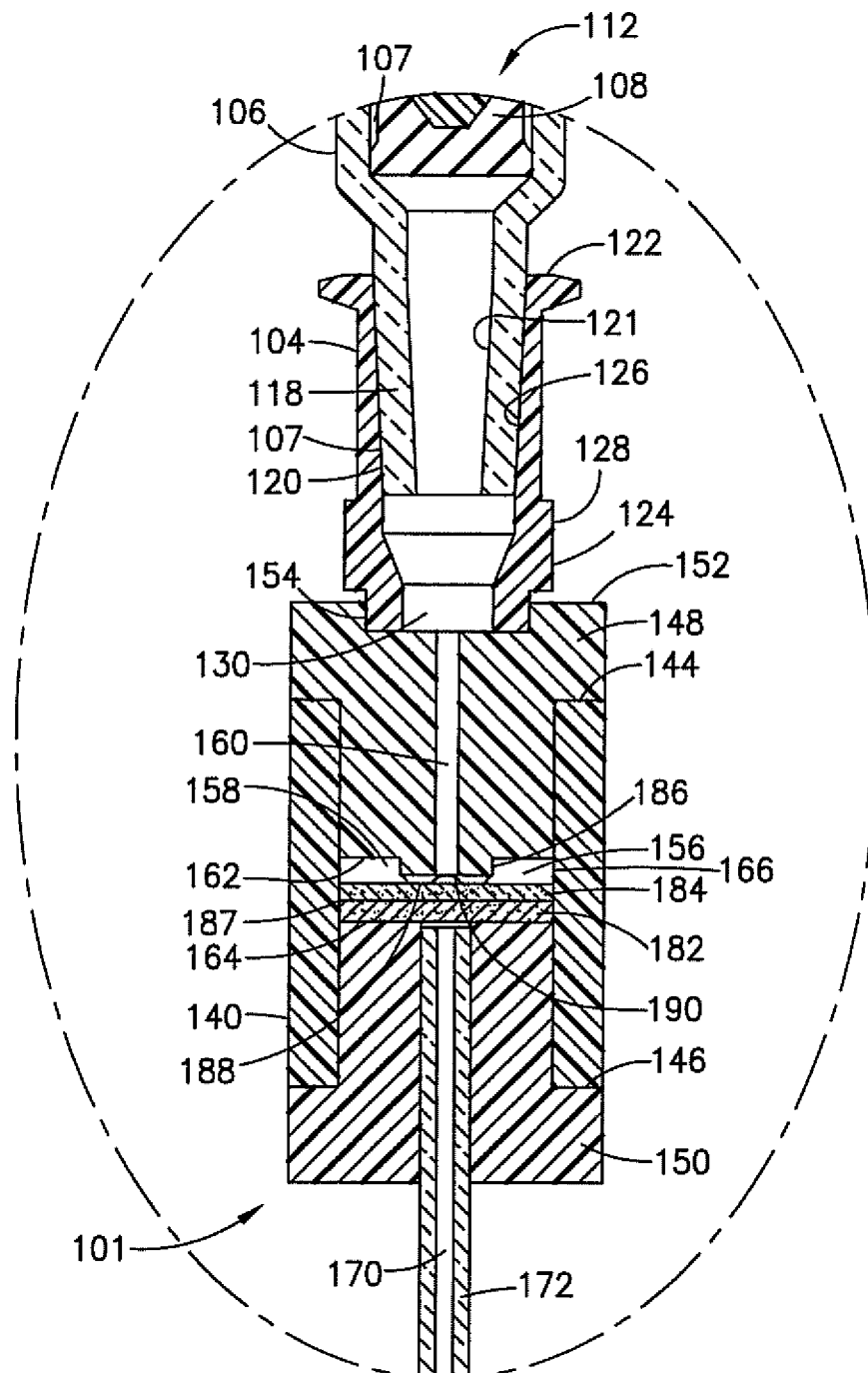
FIG. 3 is an enlarged cross-sectional view of a circled section A of FIG. 2.

FIG. 1 is a side view of an example of a nucleic acid extraction ("NAE") device 100 in accordance with an embodiment of the invention. The NAE device 100 comprises an extraction unit 101 coupled to a syringe 102 via a female port that receives a tip of the syringe. The female port 104 may be part of a Luer fitting 104, for example, as shown in the Figures. In the example of FIG. 1, the extraction unit 101 and the syringe 102, which may both comprise clear tubing, are transparent. The internal configuration of the extraction unit 101 and the syringe 102 are therefore shown. FIG. 2 is a cross-sectional view of the NAE device 100 of FIG. 1, through line 2-2 of FIG. 1, which also shows the Luer fitting 104 in cross-section. FIG. 3 is an enlarged, cross-sectional view of the circled portion A of FIG. 2.

The syringe 102 comprises a tubular body 106 defining a passage 107 and a plunger 108 having a first proximal end 110 extending outside the tubular body and a second distal end 112 movable within the passage. The first end 110 of the plunger 108 in this example has a flat, wide surface 114 and the second end 112 of the plunger includes a seal 108, as is known in the art.

A distal end 118 of the exterior of the syringe 102 is inwardly tapered toward an opening 120 through the tubular body 106. This is best shown in FIG. 3, where the distal end 118 is received within the Luer fitting 104. A portion 121 of the inner passage 107 within the distal end 118 may be inwardly tapered toward the opening 120, as well.

FIG. 3 also shows the Luer fitting 104 with a proximal end 122, a distal end 124, and an inwardly tapered inner passage 126 extending from the proximal end to the distal end, as is known in the art. A portion of the inner passage 126 includes a shoulder 127. As shown in FIG. 3, the distal end 118 of the syringe 102 is received within the proximal end 122 of the Luer fitting 104 in a tight fit providing a fluid tight seal. In this example, the inner passage 126 extends through an inwardly tapered section 128 and a straight section 130, to the distal end 124 of the Luer fitting 104.

The Luer fitting 104 may be a separate piece glued to the extraction unit 101 by acetone, for example, or the Luer fitting may be manufactured in one piece with extraction device 101. The extraction device 101 and the Luer fitting 104 may be injection molded as a one-piece unit, for example.

As best show in FIG. 3, the extraction unit 101 comprises a housing 140, which in this example comprises plastic tubing, as noted above. The housing 140 has a proximal end 144 and a distal end 146. A proximal fitting 148 is inserted into the proximal end 144 and a distal fitting 150 is inserted into the distal end 146 in a tight fit to assemble the extraction device 101. The fittings 148, 150 may be glued to the housing 140 by acetone, for example.

A proximal end surface 152 of the proximal fitting 148 defines a recessed region 154 to receive the distal end 124 of the Luer fitting 104 in a tight fit. A space 156 between the distal end 162 of the proximal fitting 148, the proximal end 164 of the distal fitting 150, and the internal walls 166 of the housing 140 defines an internal chamber 158. The internal chamber 158 is defined by the distal end 162 of the proximal fitting 148, the proximal end 164 of the distal fitting 150, and the internal walls 166 of the housing 140. The proximal fitting 158 defines a first passage 160 from the recessed region 154 to the internal chamber 158.

The distal fitting 150 defines a second passage 170 from the internal chamber 158 to a distal end of the distal fitting. A sampling tube 172 is positioned within the second passage 170. The sampling tube 172 extends from the internal chamber 158 and out the distal end 146 of the distal fitting 150.

In this example, a support, such as a porous support disc 182, is supported by the proximal end 164 of the distal fitting 150. The porous support disc 182 has an outer diameter slightly larger than an inner diameter of the internal chamber 158 so that it fits snugly within the internal chamber 158.

In accordance with this embodiment of the invention, a compliant glass fiber medium 184 configured to capture nucleic acids is supported by the porous support disc 182 or other such support, as discussed further below. The compliant glass fiber medium 184 has a first, flat position in FIG. 3, substantially filling the diameter of the internal chamber 158 to block the passage of fluid sample through the internal chamber 158. In this example, the compliant glass fiber medium 184 has an outer annular region 184a that flexes or bends into a second position in response to a vacuum created by withdrawing the plumber 108, and the resulting fluid flow, as discussed below with respect to FIG. 5. The compliant glass fiber medium 184 has an outer diameter about the same size as or slightly larger than an inner diameter of the internal chamber 158 so that it can flex, bend, or move while fluid is drawn into the NAE device 100, and fill the internal chamber when fluid is discharged from the device so that the discharging fluid is forced through the medium and cannot go around the medium.

In this example, an optional central protrusion 186 is provided in the distal surface of the proximal fitting, in contact with a proximal surface 187 of the compliant glass medium 184 in this example, to hold a center of the medium against the porous support disc 182, as shown in FIG. 3. The central protrusion 186 has a distal end surface 188 defining a passage or a groove 190 between the opening in the fluid passage 160 and an exterior edge. Alternatively, a spacer (not shown) may be provided on the distal end surface 188 of the central protrusion 186, in contact with the porous medium 184.

Figure 4:
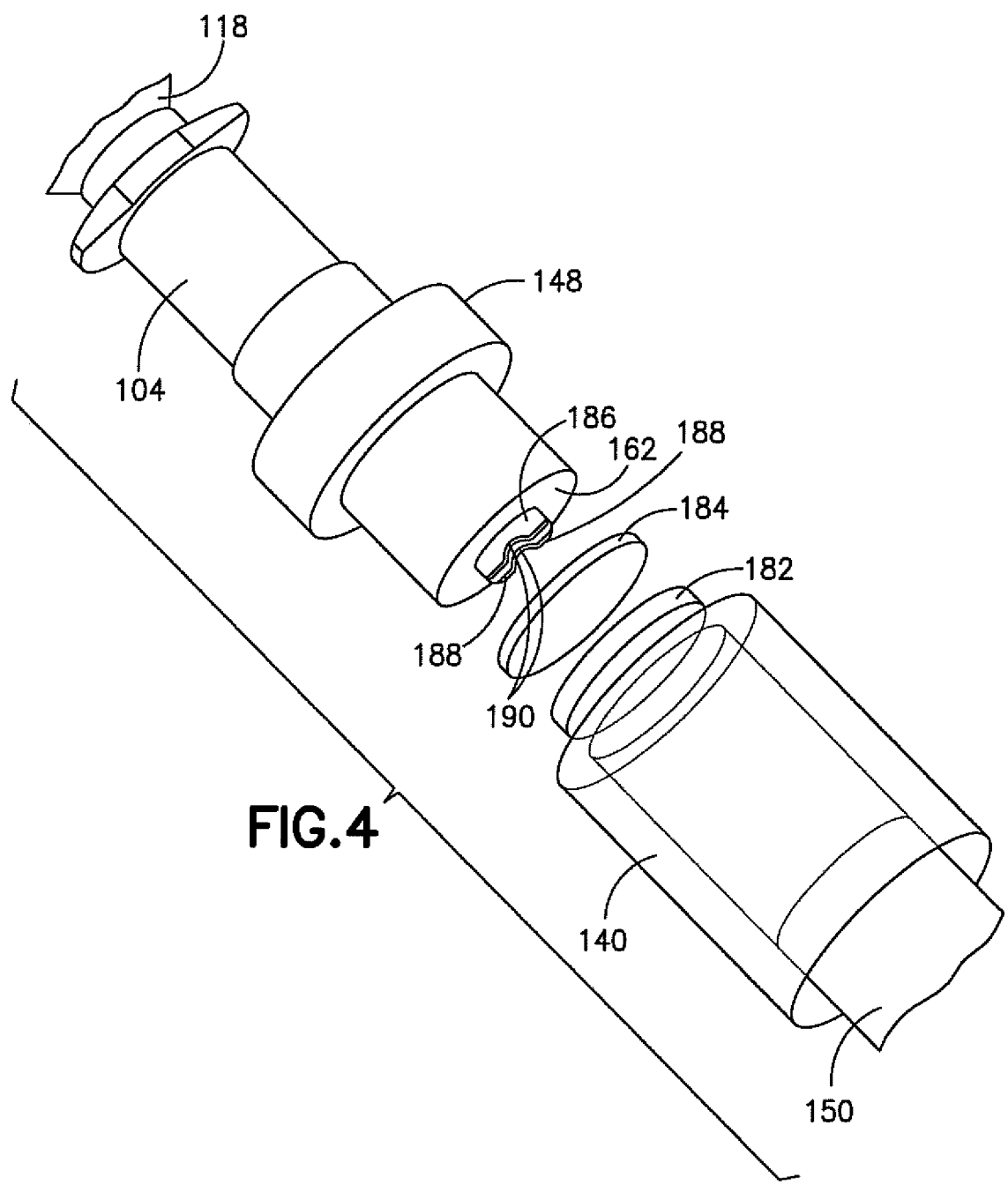
FIG. 4 is an exploded perspective view of the extraction NAE device of FIG. 1.

FIG. 4 is an exploded perspective view of the extraction unit 101, better showing the central protrusion 186. In FIG. 4, the central protrusion 186 has a circular shape and four passages 190 extending between an opening 192 of the fluid passage 160 and the exterior edge of the protrusion 186 to allow for fluid flow through the passages, into the passage 160. While four passages 190 are shown in the example of FIG. 4, more or fewer passages may be provided. FIG. 4 also shows the distal end 118 of the syringe 102, the Luer fitting 104, the proximal fitting 148, the distal fitting 150, the porous support disc 182, and the compliant glass fiber medium 184.

An example of the use of the NAE device 100 will now be described. In this example, where the Luer fitting 104 is glued to or formed in one-piece with the extraction unit 101, as discussed above, the distal end of the syringe 102 is inserted into the proximal end 122 of the Luer fitting 104 to form a tight fit, as shown in FIGS. 1-3. Initially, the plunger 108 is fully inserted into the tubular body 106, of the syringe 102 and the compliant glass medium 184 is in a first position where it is flat, fully supported by the porous support disc 182, and substantially blocking fluid flow through the internal chamber 158, as shown in FIGS. 1-3.

A distal end of the sample tube 172 is inserted into a sample of biological fluid, such as any of the biological samples listed above, for example. As discussed above, the sample fluid is lysed and/or homogenized by mixing the sample fluid with detergent in the presence of protein degrading enzymes, and mixed with a chaotropic agent, as is known in the art. The plunger 108 is then retracted toward the proximal end of the syringe, generating a vacuum in the passage 107, the internal chamber 158, the passage 170, and the sample tube 172. This causes fluid sample to be drawn from the sample, into the sample tube 172 and through the porous support disc 182, from a distal end of the NAE device 100 toward in a proximal end of the device. The fluid spreads through the porous support disc 182 as it is drawn upward through the disc, from a distal end of the internal chamber 158 to a proximal end of the internal chamber, as indicated by the arrows in the enlarged cross-sectional view of the internal chamber in FIG. 5.

The vacuum generated by withdrawal of the plunger 108 is sufficient to draw the fluid sample through the porous support disc 182 but not through the compliant glass medium 184. In one example, the vacuum pressure is up to about 14 psi when using a standard, 1 milliliter syringe. Other size syringes may be used, as well.

Since the center of the compliant glass medium 184 is secured against the porous support disc 182 by the protrusion 184, the sample fluid flow through the porous support disc 182 causes all or a portion of the outer annular region edge 184a of the compliant glass medium 184 to flex in the direction of the fluid flow, toward the proximal end of the internal chamber 158, from the first position of FIG. 3 to a flexed position, as shown in the enlarged view of the internal chamber of FIG. 5. The sample fluid therefore passes around the flexed compliant glass medium 184, through the grooves 190, and into the fluid passage 160 of the proximal fitting 148, as indicated by the arrows in FIG. 5. The sample fluid continues to be drawn in a proximal direction through the Luer fitting 104 and into the syringe body 106, rapidly filling the syringe 102, as the plunger 108 is withdrawn. It is noted that the compliant glass medium and the passages 170 and 160 may be configured and positioned so that a portion or side of the medium flexes instead of the entire annular region 184a.

After the syringe 102 is filled with sample fluid to a desired level, the plunger 108 is pushed in the distal direction into the syringe body 106, forcing the sample fluid in the distal direction through the passage 107, the Luer fitting 104, the fluid passage 160, and into the internal chamber 158 through the grooves 190. The force of the sample fluid pushes against the outer annular region 184a of the flexed compliant glass medium 184, as indicated by the arrows in the enlarged cross-sectional view of the internal chamber 158 in FIG. 6, returning the outer annular region 184a to its original position. The annular region 184a of the flexed compliant glass medium 184 also has a return force that returns the annular region to the first position from the second position when the draw force is removed.

The compliant glass medium 184 now substantially closes the internal chamber 158. Sample fluid is therefore forced through the compliant glass medium 184 under the higher discharge pressure generated by pushing the plunger 108 into the syringe 102, as is also indicated by the arrows in FIG. 6. The discharge pressure is substantially greater than pressure, such as at least about five (5) times greater, for example. The discharge pressure may be up to about 100 psi or more, for example. As the sample fluid passes through the compliant glass medium 184 in the distal direction, nucleic acids in the fluid bond to the glass fibers of the medium, while the remainder of fluid sample passes through the medium, the porous support disc 182, and the passage 170, out of the NAE device 100. The process of drawing fluid sample into the NAE device 100 and discharging the fluid sample through the compliant glass medium and out of the NAE device may be repeated multiple times with the same sample fluid to increase the amount of nucleic acids captured by the compliant glass medium 184.

After the fluid sample is expelled from the NAE device 100 the final time, a protein wash is drawn into the device 120, around the compliant glass medium 184, and then discharged through the medium, in a similar manner as discussed above with respect to the fluid sample. The protein wash contains a chaotropic agent, a buffer, and ethanol, for example. The protein wash removes proteins that may still be in the medium 184. The compliant glass medium 184 flexes from the first position to the second position as the protein wash is drawn into the NAE device 100 and then returns to the first position when the wash is discharged from the device, as discussed above with respect to fluid sample drawn into and discharged from the NAE extraction device 100.

After the first protein wash, a second wash comprising a salt, a buffer, and ethanol, for example, is drawn into the NAE device 100 to further wash the compliant glass medium 184 and to remove residual chaotropic agent that might interfere with downstream applications such as polymerase chain reaction ("PCR"), as is known in the art. The compliant glass medium 184 flexes from the first position to the second position as the second wash is drawn into the NAE device 100 to allow the second to flow past the medium and then returns to the first position as the second wash is discharged, through the medium and the device, as discussed above.

After the second wash, the nucleic acids bonded to the compliant glass medium 184 are eluted from the medium by drawing an elution buffer, such is buffered water, for example, into the device 100 and around the compliant glass medium 184, and is then discharged through the medium, as above. The buffered water passing through the compliant glass medium 154 solubilizes the nucleic acids, removing them from the medium. The discharged buffered water, which is collected in a sample container, contains the purified and concentrated nucleic acids that are ready for analysis, such as by PCR, for example.

In one example, the compliant glass medium 184 has a porosity of from about 0.20 microns to about 3 microns. In another example, the compliant glass medium 184 has a porosity of from about 0.5 microns to about 1.50 microns. In the compliant glass medium 184 described below, the medium has a porosity of about 0.7 microns.

The compliant glass medium 184 in this example may comprise silica or borosilicate glass, for example. Porex® BioDesign™ Glass Fiber Membrane, available from Porex Corporation, Fairburn, Ga., may be used for example. In one example, Grade F glass fiber is used, which is said to have a normal particle retention rating (based on 98% efficiency) of 0.7 microns, a size of 11.5 meters×11.5 meters (292 mm×292 mm), a basis weight of 65 g/m², a thickness of 450 microns, and a liquid flow rate (Modified Herzberg Method) of 315 sec/100 ml/10 cm². As is known in the art, the particle retention rating is the porosity and the basis weight is the density of the glass fiber. The glass fiber membrane may be cut with a laser cutter or punch, for example, to a desired size to fit within the internal chamber 158. Other types of compliant, woven or nonwoven fiber structures that are compliant enough to act as a check valve may be used.

The porous support disc 152 may be a porous plastic media, such as a granular material. The granular plastic material may be pressed and sintered to form a solid, porous structure that may be used as the porous support disc 152. The granular material may comprise polyethylene, nylon ABS, and other common plastics or engineered plastics. A polyethylene porous media may comprise polyethylene XS-96193 porous plastic sheet available from Porex Technologies GmbH, Aachen, Germany. XS-96193 is said to comprise XM-0269 polyethylene having a thickness of 0.60±0.10 mm, lengths of 1000 mm (minimum), width 900 mm usable area, an average pore size of 7-12 microns, edges that may be tapered, an air flow of 120-280 ml/min cm² at a set inlet pressure of 1.2" water, and a target density of 0.42-0.50 g/cm³.

Instead of the porous support disc 152, a support comprising a fiber plastic screen may be provided on the proximal end 164 of the distal fitting 150 to support the compliant glass medium. The screen may comprise nylon, for example.

Figure 7:
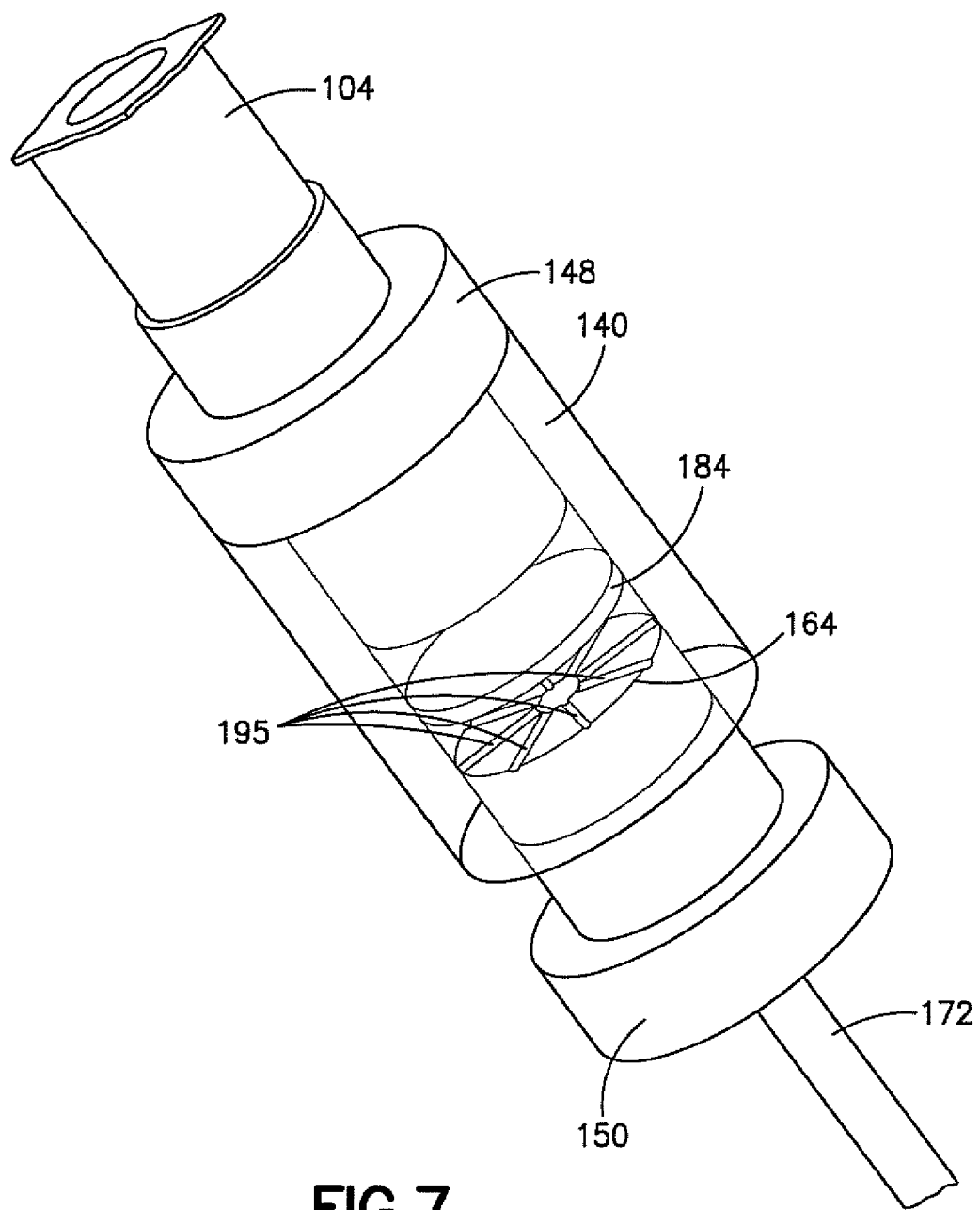
FIG. 7 is an exploded, perspective view of an NAE device in which a compliant glass medium is supported by the proximal surface of the distal fitting, in accordance with another embodiment of the invention.

In another example, the compliant glass medium 184 is supported by the proximal end 164 of the distal fitting 150. FIG. 7 is an exploded, perspective view of such a configuration, wherein elements that are the same as in FIGS. 1-6 are commonly numbered. In this example, the proximal end 164 of the distal fitting 150 has radiating grooves 195 extending from the fluid passage 160 to the edge of the proximal surface end. The grooves 195 help to evenly distribute the fluid drawn into the internal chamber 158 from the sample tubing 170 to the edge of the compliant glass medium 184. The fluid then passes by the flexed annular region 184a, around the medium 184, as discussed above and shown in FIG. 5.

When the plunger 108 is pushed into the syringe 102, forcing the fluid sample through the compliant glass medium 184 as described above, the grooves 195 guide the fluid passing through the medium to the passage 170.

The porous medium 184 may be made of other compliant flexible materials that can flex to allow fluid flow around the porous medium while the sample fluid is drawn into the syringe 102 and returns to a flat position to capture nucleic acids while the plunger 108 is pushed into the syringe 102, as discussed above.

Figure 8:
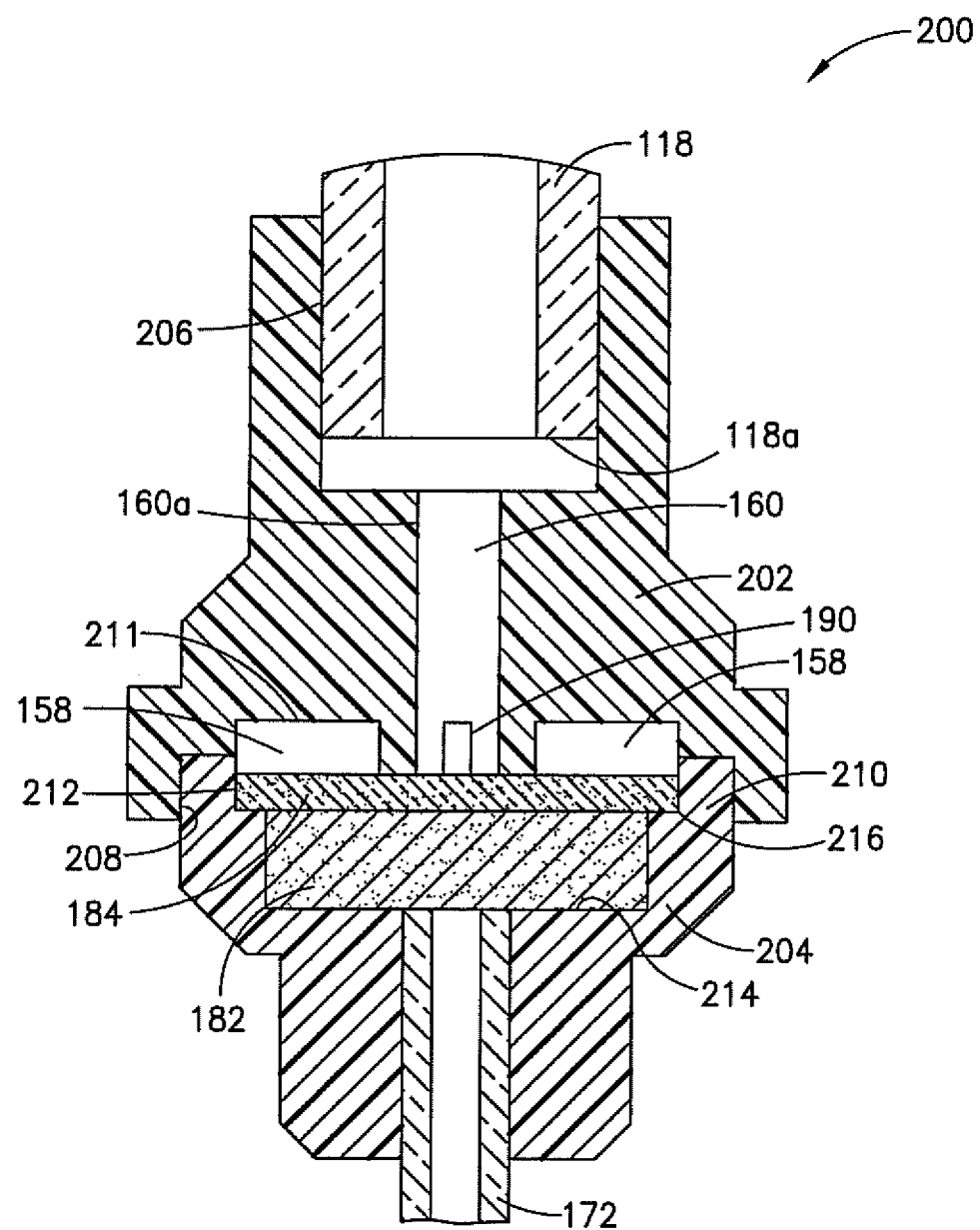
FIG. 8 is a cross-sectional view of another example of an NAE device in accordance with an embodiment of the invention that includes a female port.

FIG. 8 is a cross-sectional view of an extraction unit 200 comprising a first, proximal part 202 and a second, distal part 204. Items common to FIGS. 1-7 are commonly numbered in FIG. 8. In this example, the proximal part includes a female port 206 in a proximal end that receives the distal end 118 of the syringe in a fluid tight seal. A separate Luer fitting is not, therefore, needed. The distal tip 118a of the distal end of the syringe is placed close to the proximal opening 160a of the fluid passage 160, which reduces the carry-over of wash buffers in the elution step discussed above. Also in this example, the proximal part 202 includes a first recessed section 208 to receive a proximal portion 210 of the distal part 204 and a second recessed section 211 to define a portion of the internal chamber 158. The internal chamber 158 is also defined by first and second recessed sections 212, 214 in the proximal portion 210 of the distal part 204. Alternatively, the distal part 204 may include a proximal recessed section to receive a portion of the distal end of the proximal part 202.

The proximal and distal parts 202 204 may be glued together by acetone, for example, after placement of the porous support 182 and the compliant glass medium 182 in the recesses 214, 212 of the distal part 204.

A porous support 182 is supported in the second recessed section 214 of the distal part 204. A compliant glass media 184 is supported by the porous support 182, as well as an annular shoulder 216 in the first recessed section 121. The porous support 182 and the compliant glass medium may comprise the materials discussed above. The compliant glass medium 184 may be supported by a plastic screen instead, as discussed above.

Figure 9:
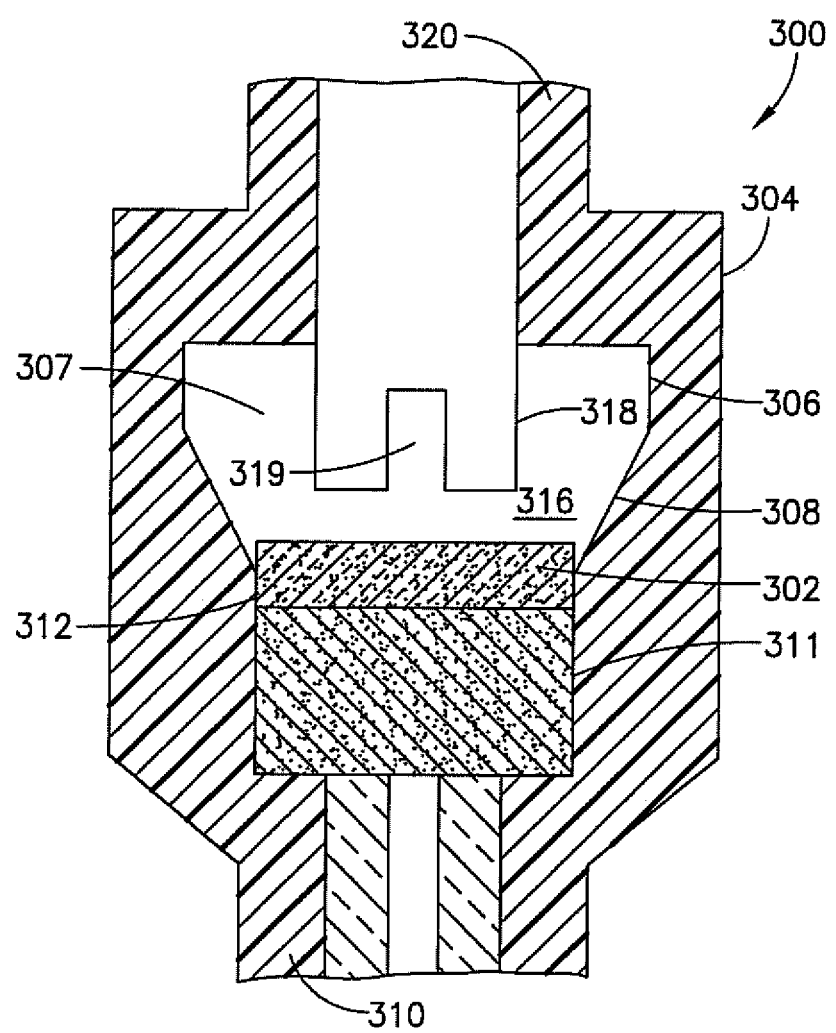
FIG. 9 is a partial cross-sectional view of a portion of another NAE device in accordance with another embodiment of the invention, showing the porous medium in a first position

FIG. 9 is a partial cross-sectional view of another NAE device 300 in accordance with an embodiment of the invention, in which a compliant or a non-compliant porous glass medium 302 may be used. The housing 304 may be the same housing as in the embodiments of FIGS. 1-6, FIG. 7, FIG. 8, FIG. 12 (described below), or another configuration. In this example, an internal wall 30 of the internal chamber 307 has a tapered portion 308 that is inwardly tapered toward the distal end of the housing 304 (outwardly tapered toward the proximal fluid passage 360). Reference is made to the embodiments of FIGS. 1-6, FIG. 7, and FIG. 8 for examples of other features of the housing 304.

In FIG. 9, the porous glass medium 408 is shown in a first position supported by an optional porous support 410. Alternatively, the porous medium may be supported by an internal surface of the housing, as in the embodiment of FIG. 7.

The porous glass medium 302 in this example is partially within a straight walled portion 312 of the wall 306. Also in this example, the porous glass medium protrudes partially into the tapered portion 316 defined by the tapered wall 308. A central protrusion 318 of a proximal portion of the housing (which may also define part of the proximal fluid passage 319 fluid path, as described above), extends into the tapered portion 316 of the internal chamber 307 and is distanced from the porous medium 302 when the porous medium is in the first position of FIG. 9.

Figure 10:
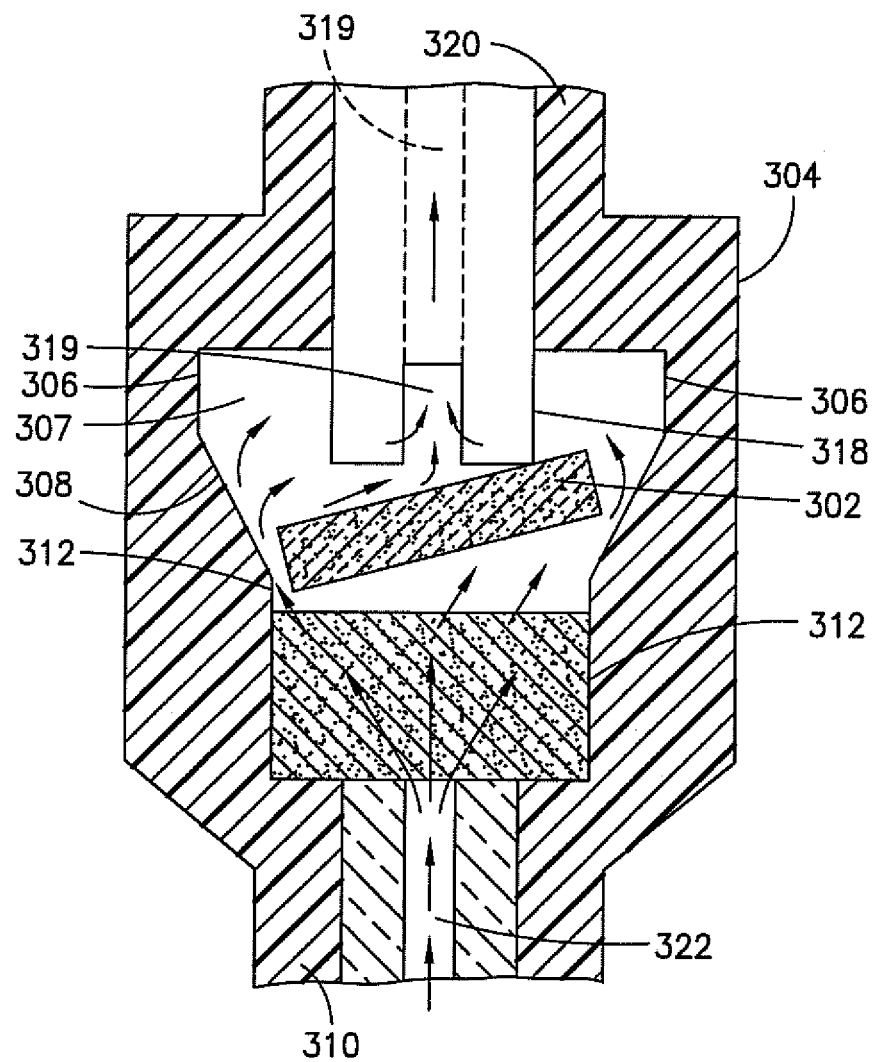
FIG. 10 is a cross-sectional view of the embodiment of FIG. 9, showing the porous medium in or moving toward a second position.

FIG. 10 shows the movement of the porous glass medium when fluid is drawn into the housing 304, from a distal open end 310, though a distal fluid passage 322, toward the proximal open end 320 of the housing. Since the central protrusion 318 does not bear against the porous medium 302 and the porous medium does not fit tightly within the wall 312, as above, the porous medium is free to move toward the central protrusion when fluid is drawn into the housing toward the proximal end 320. As the porous medium 302 moves toward the central protrusion 318, into the tapered portion 316, an open space develops between the periphery of the porous medium and the straight wall portion 312 and the tapered wall portion 306, allowing fluid to flow around the porous medium, into the proximal fluid passage through the bottom and side openings 319 of the central protrusion 318. The porous medium 302 may tilt as it is moved toward the central protrusion 318, as shown in FIG. 10. As fluid continues to be drawn into the housing 304, the porous medium 302 may straighten as it engages the central protrusion 318. The porous medium may also move straight toward the central protrusion 318 without tilting.

Figure 12:
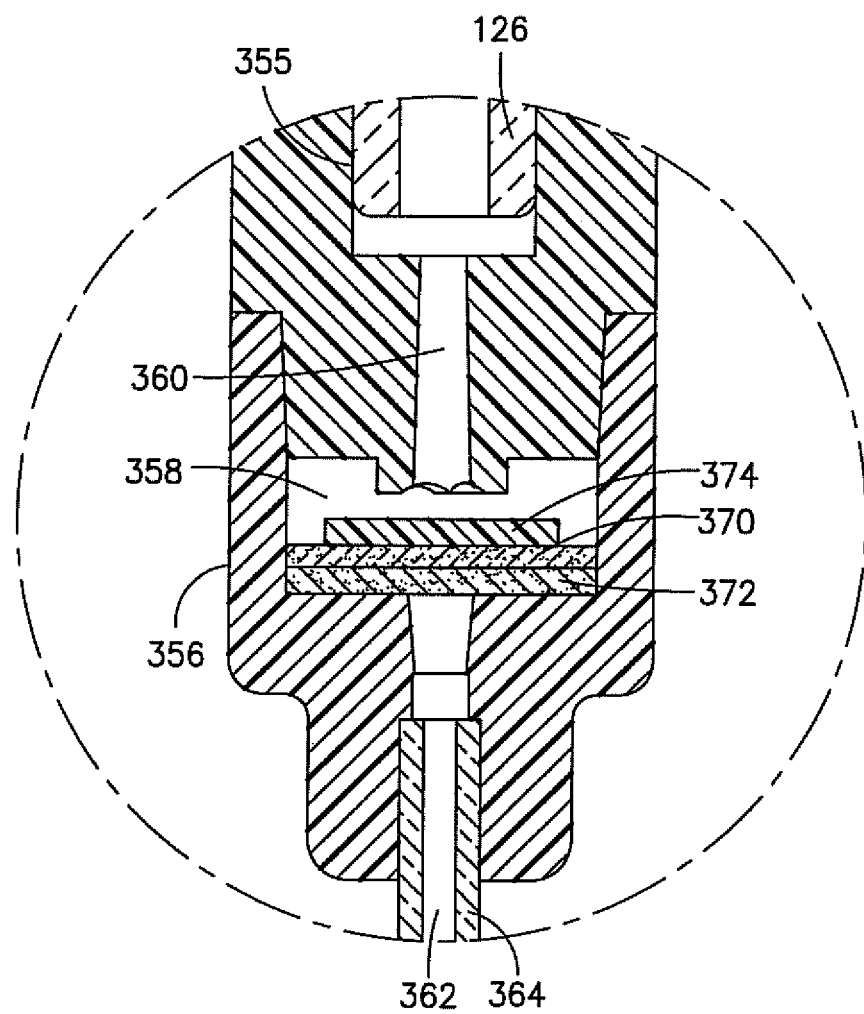
FIG. 12 is an enlarged, cross-sectional view of the circled region B of FIG. 11, showing a plastic disk and a porous medium in a first position.
Figure 13:
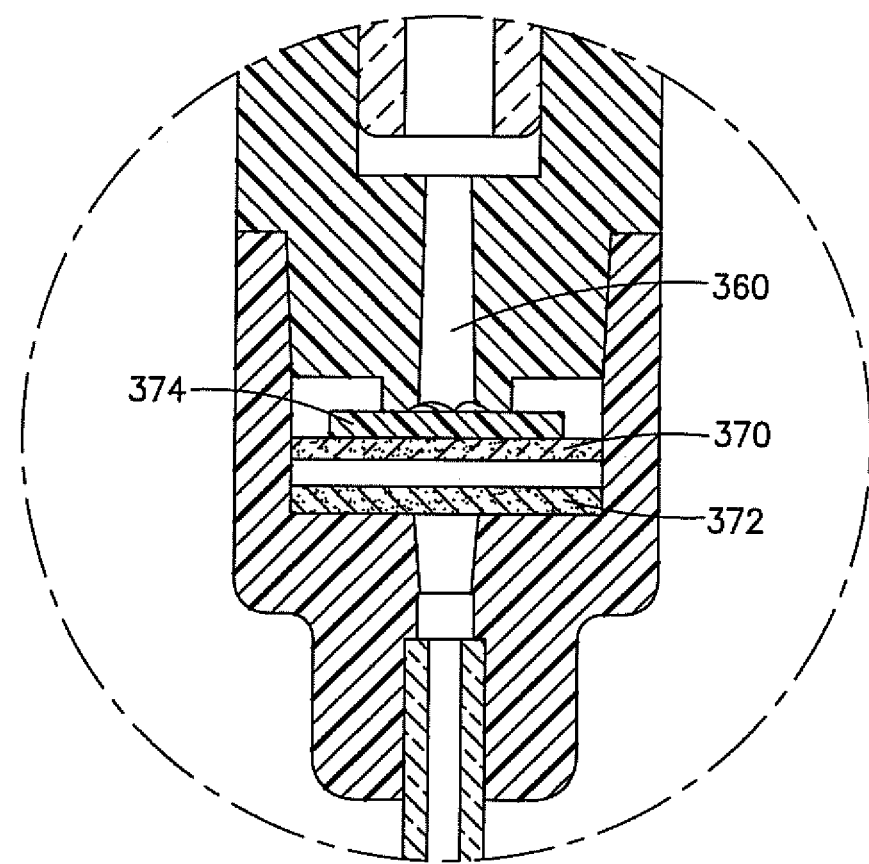
FIG. 13 is an enlarged cross-sectional view as in FIG. 12, showing the plastic disk and the porous medium in a second position.

As above, a spacer (not shown) may be provided at the end of the central protrusion 318, which may contact the porous medium 302 when the medium is moved toward the protrusion. Alternatively, the central protrusion 318 may be close enough to the porous medium 302, but still spaced from it, so that the porous medium tilts or moves sufficiently to provide a space for fluid flow between the straight wall portion 312 and the tapered portion 308 without completely entering the tapered wall portion 316. An example of such an embodiment is shown in FIGS. 11-13.

When fluid is discharged toward the distal open end and out of the housing 304, the porous medium 302 moves back to the first position, as shown in FIG. 9. The tapered wall 306 guides the porous medium 302 back to the first position against the porous support 310, preventing fluid flow around the porous medium. The fluid then flows through the porous medium 302 and porous support 310, if present, and into the distal fluid passage 322 and out of the housing 304. Nucleic acids in the fluid are captured in the porous medium 302, as described above. Also as described above, fluid sample may be drawn into and discharged from the housing multiple times. Also as described above, nucleic acids may be eluted from the porous medium 408 by the one or more washes described above.

A non-compliant porous medium 408 may comprise a non-compliant glass material, such as sintered glass, for example, with a porosity in the ranges described above. If the porous medium 302 is compliant, it may comprise glass fiber as described above.

Figure 11:
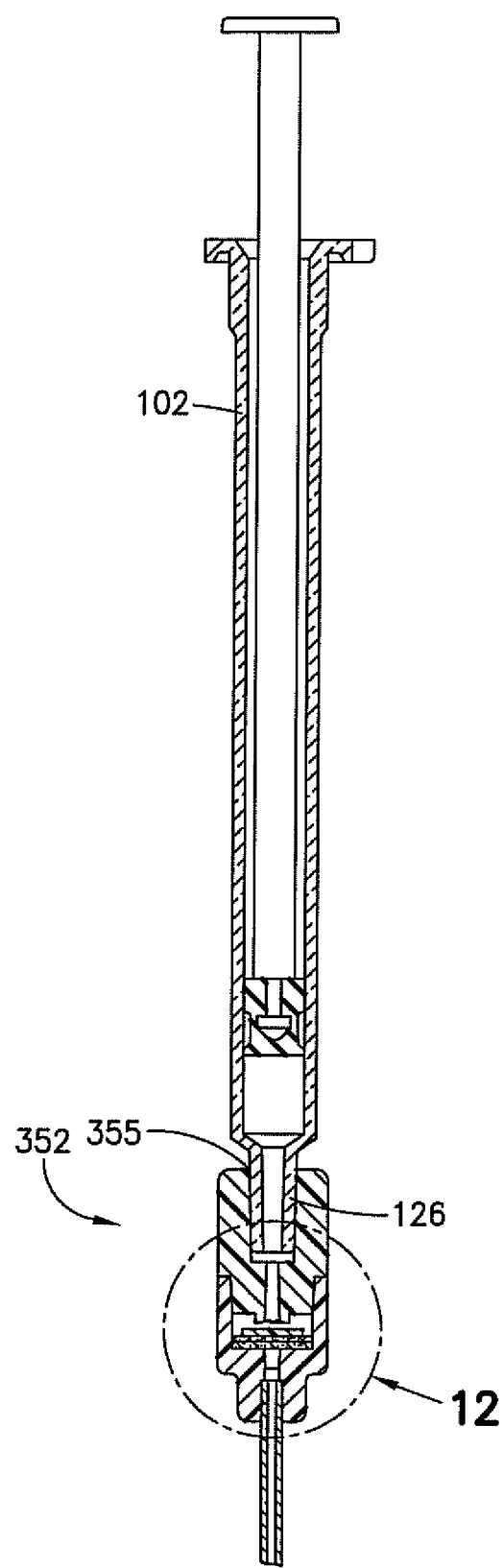
FIG. 11 is a cross-sectional view of another NAE extraction device in accordance with another embodiment.

FIG. 11 is a cross-sectional view of another embodiment 350 of the invention. The syringe 102 is the same as the syringe in FIGS. 1 and 2. FIG. 12 is an enlarged cross-sectional view of the circled region B of FIG. 11. The NAE extraction device 352 in this example includes a proximal fitting 354 and a distal fitting 356 bonded to each other to define an internal chamber 358, as in the embodiment of FIG. 8. The proximal fitting 354 defines a proximal open end 355 configured to receive a distal tip 126 of the syringe 102.

The proximal fitting 354 defines a proximal fluid passage 360 and distal fitting defines a distal fluid passage 362, both of which being in fluid communication with the internal chamber 358. A distal sample tube 364 extends from the distal fluid passage 362, for insertion into a fluid sample, as discussed above.

The proximal fitting 354 in this example has an optional central protrusion 366 that protrudes into the internal chamber 358, the proximal fluid passage 360 extends through the central protrusion 366, to the internal chamber. Sides of the central protrusion 366 may have partially cut out portions 368 to enable entry of fluid into the proximal fluid passage 360 from the side of the central protrusion.

A compliant porous glass medium 370 is supported by a porous support 372 within the internal chamber 358. The porous medium 370 may comprise glass fibers and the porous support may comprise plastic, as discussed above.

In this embodiment, a porous plastic disk or member 374 is provided on the porous filtration medium 370, as shown in FIG. 12. The porous plastic disk may be free floating within the internal chamber 358. When fluid is drawn into the NAE device 352, the porous plastic disk 374 is drawn toward and into contact with the central protrusion 366 and the porous medium 370 is drawn from a first position shown in FIG. 12 toward and into contact with the disk, in a second position shown in FIG. 13. The porous plastic disk 374 may improve fluid flow into the proximal fluid passage by preventing the glass fibers of the porous medium 370 from clogging the side and/or bottom openings to the proximal fluid passage. Since the disk 374 is porous, fluid may flow through the disk 374, into the proximal fluid passage 360, as well as around the disk and through the passages or grooves 368, while fluid is drawn into the device 352. The disk may also be non-porous, in which case fluid would only flow into the proximal fluid passage 360 through the passages or grooves 368. The clogging problem may be prevented or mitigated by other methods, such as by making the side cut outs 368 and/or bottom openings larger, and/or by making the side passages or grooves taller, for example. If a central protrusion is not provided, the disk may or may not be provided to prevent clogging of an entrance to the proximal fluid passage 360 from the internal chamber 358.

The porous plastic disk 374 may be used in the other embodiments described above. In the embodiments of FIGS. 1-7 and 8, where the central protrusion bears against the porous filtration medium, the plastic disk 374 may be provided between the central protrusion and the porous filtration medium. In these cases, the porous plastic disk 374 acts as a spacer between the central protrusions and the porous filtration medium. The porous plastic disk 374 may also be used in the embodiment of FIGS. 9-10, in a similar manner as in the current embodiment.

The disk 370 may be the same material as the porous support 372 or a different material.

The internal walls of the internal chamber are inwardly tapered toward the distal 362 (outwardly tapered toward the proximal fluid passage 360), to facilitate movement of the porous glass medium 370 and passage of fluid around the medium when fluid is drawn into the device. It also serves to guide the porous medium 370 back into position filling the internal chamber 358 during discharge of fluid.

Figure 14:
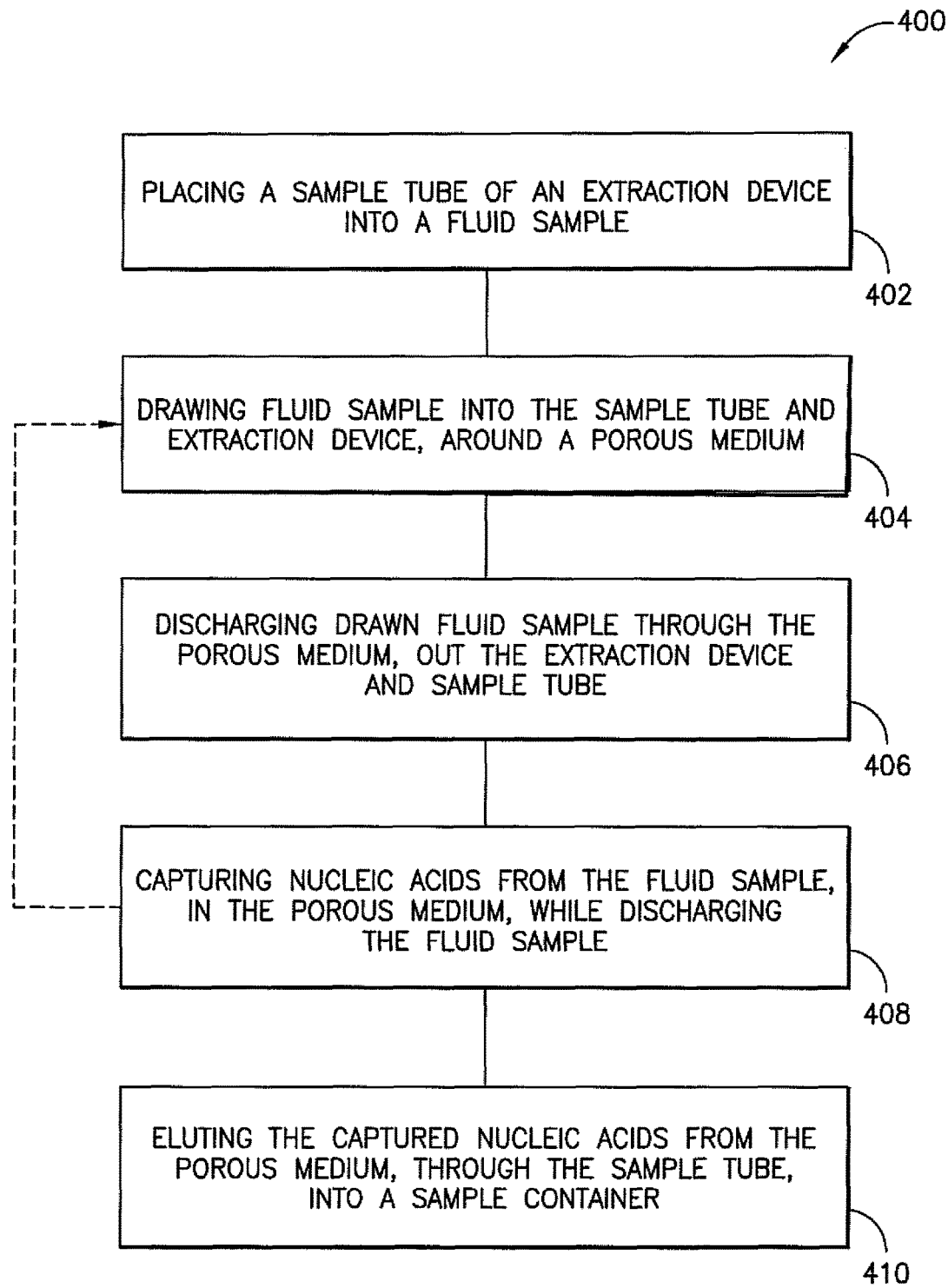
FIG. 14 is a flowchart of a method in accordance with an embodiment of the invention.

FIG. 14 summarizes an example of a method 400 of extracting nucleic acids from a fluid sample in accordance with an embodiment of the invention. In this example, a sample tube of an extraction device in accordance with an embodiment of the invention, is inserted into a fluid sample, in Step 402.

Fluid is drawn through the sample tube, into the extraction device, by applying a vacuum to a proximal end of the extraction device in accordance with an embodiment described herein, in Step 404. The vacuum causes a compliant porous medium within a fluid passage of the device to move, such as by bending, tilting, or displacing, allowing fluid flow around the porous medium, into the internal chamber and proximal fluid passage of the device. The vacuum may be applied by a syringe or a pipette, for example.

After sufficient fluid is drawn into the extraction device, a discharge force is applied to the fluid passage, forcing the fluid to flow toward the sample tube and out of the device and tube, in Step 406. The fluid moving toward the porous medium moves the porous medium into a flat position, filling the internal chamber, so that the fluid cannot pass around the medium. The discharge force is sufficient to force the fluid through the porous medium. The discharge force may be applied by pushing the plunger of the syringe into the syringe or reversing the pressure on the pipette, for example.

The porous medium captures nucleic acids in the fluid forced through the medium, in Step 408. Steps 404-408 may be repeated a desired number of times.

After Steps 404-408 are performed the desired number of times, the captured nucleic acids are eluted from the porous medium, through the sample tube, and into a sample container, in Step 410. Elution may be provided by drawing an elution buffer into the sample tube and device, around the porous medium, as discharging the elution buffer, through the porous medium, as described above with respect to Steps 402-408. One or more washes may be drawn and discharged as described above with respect to Steps 402-408, prior to drawing/discharging the elution buffer, as described above.

While the embodiments above include a syringe and a sampling tube, the extraction unit 101 may be incorporated into a pipette, such as an electronic pipette, a robotic pipetter, a manual pipetter including a bulb, for example, or other pressure sources configured to draw fluid through the extraction device in a first direction and expel fluid through the extraction device in a second direction.

Figure 15:
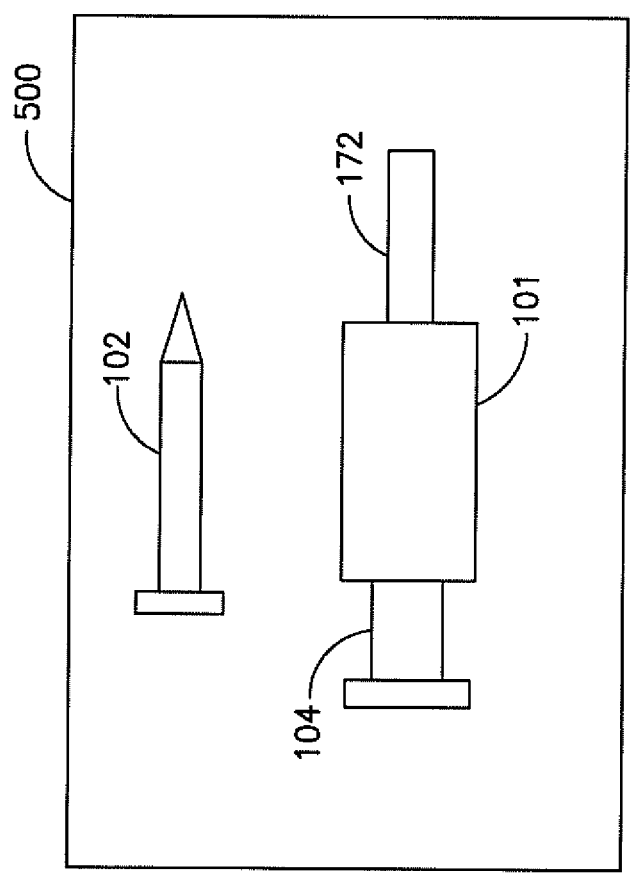
FIG. 15 is a top view of a kit comprising a syringe and an extraction/preparation device, in accordance with another embodiment of the invention.

The NAE device 100 may be provided in a kit 500 comprising the syringe 102, the Luer fitting 104, if needed, and the NAE unit 101, as shown in FIG. 15. The NAE unit may comprise any of the configurations described above, for example. As discussed above, the Luer fitting 104 and the NAE unit 101 may be bonded together or formed as a one-piece unit. The syringe 102 is provided as a separate unit in this example. Additional material may be provided in the kit, such as disposable pipettes, containers of the various buffers and/or washes described above, and collection containers, for example.

It will be appreciated by those skilled in the art that changes may be made to the embodiments described herein, without departing from the spirit and scope of the invention, which is defined by the following claims.

What is claimed is:

1. A method of extracting materials from a fluid, comprising:
   (a) providing a fluid extraction device having a housing comprising a fluid passage and a porous medium freely movable in said fluid passage, wherein said porous medium is capable of moving, relative to said housing, between a first position to open a space adjacent to said porous medium and a second position to close said space adjacent to said porous medium;
   (b) directing fluid into said fluid passage through said space adjacent to said porous medium, wherein upon directing said fluid into said fluid passage, said porous medium is positioned in said first position; and
   (c) discharging said fluid from said fluid passage through said porous medium, wherein upon discharging said fluid from said fluid passage, (1) said porous medium is positioned in said second position, thereby closing said space adjacent to said porous medium, and (2) said porous medium captures nucleic acids from said fluid.

2. The method of claim 1, wherein said porous medium moves between said first position and said second position upon deformation of at least a portion of said porous medium.

3. The method of claim 1, wherein said porous medium moves between said first position and said second position by translation.

4. The method of claim 1, wherein said fluid is directed into said fluid passage using a draw pressure, wherein said fluid is discharged from said fluid passage using a discharge pressure, and wherein said discharge pressure is greater than said draw pressure.

5. The method of claim 1, wherein said porous medium comprises at least one material selected from the group consisting of silica, borosilicate, polyethylene, nylon, and Acrylonitrile-Butadiene-Styrene (ABS).

6. The method of claim 1, wherein said porous medium comprises glass and polyethylene.

7. The method of claim 1, wherein said porous medium comprises two or more portions.

8. The method of claim 7, wherein said two or more portions of said porous medium comprises a first portion and a second portion, wherein said first portion comprises glass, and wherein said second portion comprises a polymer.

9. The method of claim 1, further comprising, after discharging said fluid, repeating (b) and (c) for a given number of cycles thereby capturing a remainder of said nucleic acids from said fluid.

10. The method of claim 1, further comprising after discharging said fluid:
    (a) directing a wash buffer into said fluid passage through said space adjacent to said porous medium; and
    (b) discharging said wash buffer from said fluid passage through said porous medium, wherein upon discharging said wash buffer from said fluid passage, said porous medium captures nucleic acids from said wash buffer.

11. The method of claim 1, further comprising eluting said nucleic acids from said porous medium.

12. The method of claim 11, wherein said eluting is performed using an elution buffer selected from the group consisting of water, tris(hydroxymethyl)aminomethane-ethylenediaminetetraacetic acid (Tris-EDTA), or a combination thereof.

13. The method of claim 1, wherein said porous medium has a porosity from about 0.2 microns to 3 microns.

14. The method of claim 1, wherein said fluid extraction device further comprises a proximal fitting, a distal fitting, and a chamber therebetween, wherein said chamber is in fluid communication with said fluid passage, wherein said chamber comprises a proximal surface and a distal surface, and wherein said chamber comprises said porous medium.

15. The method of claim 14, wherein at least one of said proximal surface and said distal surface comprises one or more grooves that distribute said fluid in said chamber upon flow of said fluid towards said chamber.

16. The method of claim 14, wherein at least one of said proximal surface and said distal surface comprises one or more grooves that prevent said porous medium from blocking said fluid passage.

17. The method of claim 14, wherein said chamber further comprises a lateral surface, wherein at least a portion of said lateral surface comprises a taper relative to a longitudinal axis of said fluid passage.

18. The method of claim 17, wherein a distal end of said lateral surface comprises said taper.

19. The method of claim 17, wherein a size of said space adjacent to said porous medium is based at least in part on an angle of said taper.

20. The method of claim 14, wherein said fluid passage comprises a protruding portion that protrudes into said chamber, wherein said porous medium, in said first position, abuts said protruding portion, thereby opening said space adjacent to said porous medium.

21. The method of claim 14, wherein an axial cross-section of a distal portion of said chamber is substantially similar to an axial cross-section of said porous medium, and wherein during discharging said fluid, said porous medium is positioned such that said space adjacent to said porous medium is closed and said fluid passes through said porous medium.

22. The method of claim 1, wherein said fluid is directed into said fluid passage using a draw pressure, which draw pressure is applied using a syringe.

23. The method of claim 1, wherein said fluid passage is in fluid communication with a source of pressure.

24. The method of claim 1, wherein said fluid extraction device further comprises a tip with an opening in fluid communication with said fluid passage.

25. The method of claim 1, wherein said porous medium comprises glass.

26. The method of claim 1, wherein said porous medium comprises a polymer.

* * * * *